(12) United States Patent
Zheng et al.

(10) Patent No.: US 11,872,383 B2
(45) Date of Patent: Jan. 16, 2024

(54) FLEXIBLE SHAFT STRUCTURE INSULATING WEAR PARTICLES BY PERFUSION

(71) Applicant: FORQALY MEDICAL(SHANGHAI) CO., LTD., Shanghai (CN)

(72) Inventors: Qiwen Zheng, Shanghai (CN); Zhirong Tang, Shanghai (CN)

(73) Assignee: FORQALY MEDICAL(SHANGHAI) CO., LTD., Shanghai (CN)

( * ) Notice: Subject to any disclaimer, the term of this patent is extended or adjusted under 35 U.S.C. 154(b) by 701 days.

(21) Appl. No.: 17/078,841

(22) Filed: Oct. 23, 2020

(65) Prior Publication Data

US 2021/0113752 A1 Apr. 22, 2021

Related U.S. Application Data

(63) Continuation of application No. PCT/CN2020/089427, filed on May 9, 2020.

(30) Foreign Application Priority Data

Oct. 17, 2019 (CN) .......................... 201910985742.7

(51) Int. Cl.
*A61M 60/408* (2021.01)
*F16C 1/24* (2006.01)
*A61M 60/857* (2021.01)

(52) U.S. Cl.
CPC ........ *A61M 60/408* (2021.01); *A61M 60/857* (2021.01); *F16C 1/24* (2013.01);

(Continued)

(58) Field of Classification Search
CPC . A61M 60/408; A61M 60/411; A61M 60/414
See application file for complete search history.

(56) References Cited

U.S. PATENT DOCUMENTS 7,022,100 B1 * 4/2006 Aboul-Hosn ....... A61M 60/865
604/6.11

* cited by examiner

Primary Examiner — George R Evanisko
(74) *Attorney, Agent, or Firm* — IPRO, PLLC

(57) ABSTRACT

The present invention discloses a flexible shaft structure insulating wear particles by perfusion, which includes a flexible transmission shaft, a proximal holder is provided at one end of the flexible transmission shaft, a distal holder is provided at the other end of the flexible transmission shaft, a constraint insulator and an outer sheath tube are provided outside the flexible transmission shaft, and the constraint insulator sequentially includes an inner constraint layer, an insulation layer and an outer constraint layer from inside to outside; a perfusion inflow annular cavity is formed between the outer constraint layer and the outer sheath tube and between the outer constraint layer and the insulation layer, respectively, and a static sealed inner cavity is formed between the inner constraint layer and the insulation layer and between the inner constraint layer and the flexible transmission shaft, respectively; the proximal holder is provided with a perfusion inlet pipeline communicated with the perfusion inflow annular cavity and a perfusion exhaust pipeline communicated with the static sealed inner cavity; and the distal holder is provided with a perfusion insulation cavity. According to the present invention, the generated wear particles can be effectively insulated, the stability and consistency of perfusion flow of the product are improved, and the problems of vibration and noise of the flexible shaft under high-speed rotation are solved.

8 Claims, 2 Drawing Sheets

(52) U.S. Cl.
CPC ............... *A61M 2205/366* (2013.01); *A61M 2205/3606* (2013.01); *A61M 2205/3633* (2013.01); *A61M 2205/42* (2013.01)

FLEXIBLE SHAFT STRUCTURE INSULATING WEAR PARTICLES BY PERFUSION

TECHNICAL FIELD

The present invention relates to a torque transmission structure in an interventional blood pumping catheter device for realizing an external power source, more particularly, to a flexible shaft structure insulating wear particles by perfusion.

BACKGROUND ART

Flexible shaft drive structures are widely used in different fields, but usually provide quite different main features in different fields. For example, large flexible shaft structures applied in the field of machine tools and fans may operate at lower rotating speeds but have to transmit higher torques; micro flexible shaft structures known in the dental field have to operate at very high speeds but only to transmit lower torques; those in the field of interventional instruments, such as intravascular ultrasound catheters, require compliance with complex twisting structures, but have only to transmit lower speeds and torques. Vibration and wear are common challenges in the use of flexible shafts, especially in high-speed applications, and strengthened constraints, addition of lubricants and improved centering are common improvements to different structures. Moreover, in the application of interventional instruments, insulation of wear particles is a unique technical challenge in the clinical application, and perfusion flushing is a common approach of improvement to wear control.

Patent document CN102711860A discloses a flexible shaft structure, wherein sliding friction relationship points between a shaft and a sleeve are defined by adding sleeve structures closely attached to the shaft and arranged at regular intervals, so that sliding friction is reduced while vibration of the shaft is suppressed.

Patent document WO2011/139248A2 discloses a flexible shaft support structure wherein the flexible shaft is ensured to remain centered during operation by adding at least one bearing component to the shaft and housing, thereby reducing the generation of wear particles.

Patent document CN105917118A discloses a perfusion flushing structure for controlling, by two perfusion pumps, a flow state of a perfusate in a catheter, to flush wear particles out of a product, thereby preventing the wear particles from entering a patient.

As can be seen from the above, the main technical solutions in the aspect of vibration and noise improvement in the prior art can be classified as two types, one type is to strengthen the constraint on the rotating shaft to ensure that the rotating shaft can still be kept centered under different bending conditions, and the other type is to reduce the friction in the operation of the rotating shaft by different constraint structures. However, the improvement solutions in the prior art cannot be directly applied in the field of interventional medical devices. On one hand, mature technical solutions in the industrial field require a large transmission structure with an outer diameter at least not smaller than 10 mm, so the prior art cannot be applied to interventional medical devices. On the other hand, the mature technical solutions now available focus more on the transmission torque, with the supportable minimum bending radius being often relatively large and the bendable degree being generally smaller than 90°, and thus fail to satisfy the specification limit of sterile packaging of medical devices and the use context featuring complex bent channels in an interventional operation.

In addition, the control solution of flushing in the prior art is arrived at through additional perfusion control approaches and state monitoring solutions to render more accurate and controllable perfusion flow on the basis of the well-known method of flushing to remove wear particles, to satisfy the requirement of accurate measurement of the perfusate clinically. However, according to the technical solution, collaboration of two perfusion pumps and a plurality of sensors is necessary to realize precise flow control, complexities in the structure and the control algorithm lead to difficulties in implementation and high costs. Furthermore, the technical solution, which in essence adopts still flushing removal, consumes extra perfusate. Unlike the industrial environment where only cooling water is required, the medical perfusate has special composition and sterile requirements, so the extra consumption of the perfusate also means extra costs of consumables.

SUMMARY OF THE INVENTION

It is an object of the present invention to solve the technical problem in the prior art by providing a flexible shaft structure insulating wear particles by perfusion, which can supply cooling/lubricating liquid to a flexible transmission shaft, effectively insulate generated wear particles, prevent the wear particles from entering a patient body, improve the stability and consistency of perfusion flow of the product, and reduce vibration and noise of the flexible shaft under high-speed rotation.

The technical solution adopted by the present invention to solve the technical problem is to provide a flexible shaft structure insulating wear particles by perfusion, including a flexible transmission shaft, a proximal holder being provided at one end of the flexible transmission shaft, and a distal holder being provided at the other end of the flexible transmission shaft, wherein a constraint insulator and an outer sheath tube are provided outside the flexible transmission shaft, and the constraint insulator sequentially includes an inner constraint layer, an insulation layer and an outer constraint layer from inside to outside; a perfusion inflow annular cavity is formed between the outer constraint layer and the outer sheath tube and between the outer constraint layer and the insulation layer, respectively, and a static sealed inner cavity is formed between the inner constraint layer and the insulation layer and between the inner constraint layer and the flexible transmission shaft, respectively; the proximal holder is provided with a perfusion inlet pipeline communicated with the perfusion inflow annular cavity and a perfusion exhaust pipeline communicated with the static sealed inner cavity; the distal holder is provided with a perfusion insulation cavity through which the flexible transmission shaft passes.

Compared with the prior art, the present invention has the advantages of: (1) supply of cooling or lubricating fluid to a flexible transmission shaft; (2) a complete insulation of particles generated in the operation process of the flexible transmission shaft; (3) the ensured stability of distal perfusion, and then the ensured reliability of distal perfusion sealing and the controllability of actual perfusion flow; and (4) reduced noise and vibration of the flexible transmission shaft under high-speed rotation.

Figure 1:
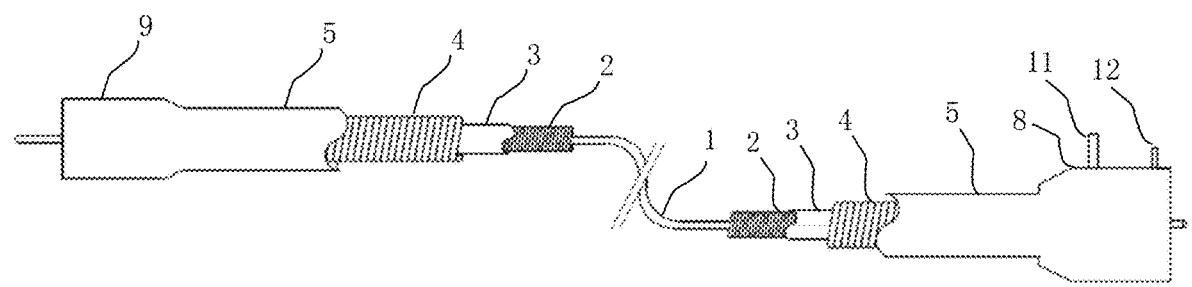
FIG. 1 is a schematic view showing a structure of a flexible shaft in an embodiment of the present invention.

In the drawings:
1 Flexible transmission shaft
2 Inner constraint layer
3 Insulation layer
4 Outer constraint layer
5 Outer sheath tube
6 Static sealed inner cavity
7 Perfusion inflow annul cavity
8 Proximal holder
9 Distal holder
10 Perfusion insulation cavity
11 Perfusion inlet pipeline
12 Perfusion exhaust pipeline
13 Threaded cut section
14 Polymer sealing layer

DETAILED DESCRIPTION OF THE INVENTION

The present invention will now be further described with reference to the drawings and examples.

Figure 2:
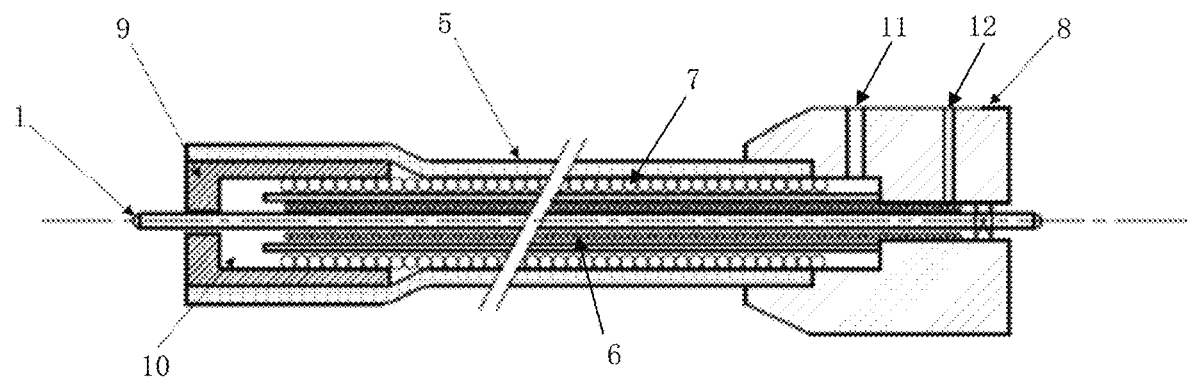
FIG. 2 is a schematic view showing an axial sectional structure of the flexible shaft along a flexible transmission shaft in an embodiment of the present invention.
Figure 3:
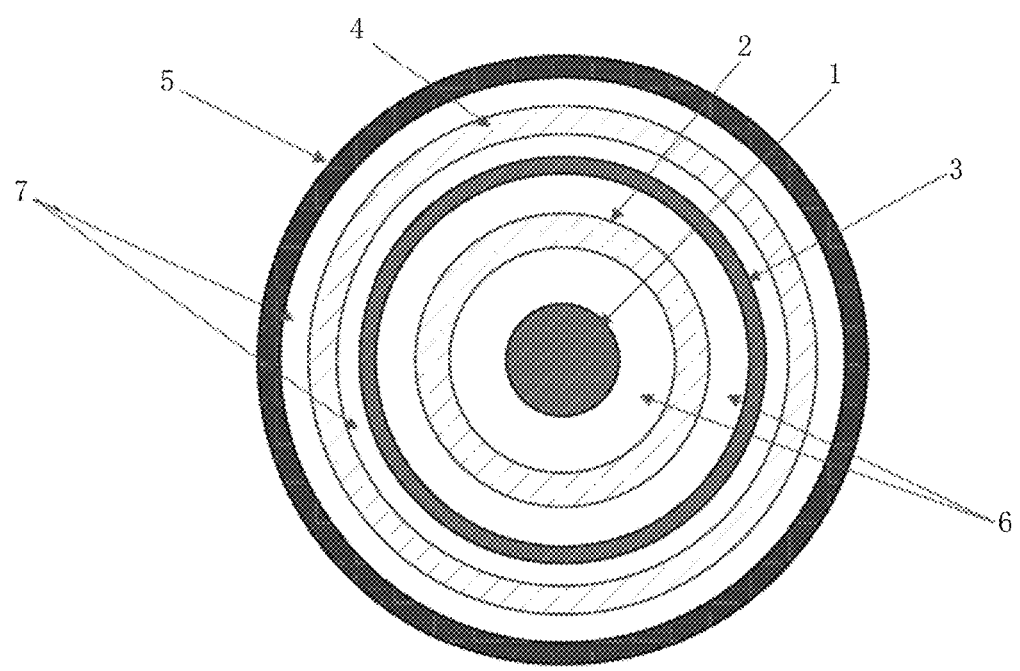
FIG. 3 is a schematic view showing a radial enlarged sectional structure of the flexible shaft along the flexible transmission shaft in an embodiment of the present invention.

FIG. 1 is a schematic view showing a structure of a flexible shaft in an embodiment of the present invention; FIG. 2 is a schematic view showing an axial sectional structure of the flexible shaft along a flexible transmission shaft in an embodiment of the present invention; FIG. 3 is a schematic view showing a radial enlarged sectional structure of the flexible shaft along the flexible transmission shaft in an embodiment of the present invention.

Referring to FIGS. 1, 2 and 3, the present invention provides a flexible shaft structure insulating wear particles by perfusion, including a flexible drive shaft 1, a restraint insulator, an outer sheath tube 5, a distal holder 9 and a proximal holder 8.

The flexible drive shaft 1 is connected at its distal end with a rotating element of a blood pump intended to be used and at its proximal end to a driving power means intended to be used. The proximal holder 8 is wrapped around the outer sheath tube 5 and the constraint insulator; the distal holder 9 may also be wrapped around the outer sheath tube 5 and the constraint insulator or snugly disposed within the outer sheath tube 5.

The constraint insulator is composed of an insulation layer 3, an inner constraint layer 2 and an outer constraint layer 4. The inner restraint layer 2 is composed of at least one braided spring tube or flexible metal tube coaxial with the flexible transmission shaft 1, and the outer restraint layer 4 is composed of at least one braided spring tube or flexible metal tube coaxial with the insulation layer 3. Weights of the braided spring tubes composing the inner and outer restraint layers increase gradually from inside to outside. The insulation layer 3 is composed of a flexible metal tube or a multilayer braided tube capable of insulating liquid coaxial with the inner constraint layer 2.

The outer sheath tube 5 is connected with the distal holder 9 and the proximal holder 8 to form a closed pipeline for accommodating the flexible transmission shaft 1, the constraint insulator and a perfusate. The outer sheath tube 5, the outer restraint layer 4, the insulation layer 3 and the proximal holder 8 form a perfusion inflow annular cavity 7, through which the perfusate finally enters a patient body. The insulation layer 3, the inner constraint layer 2 and the proximal holder 8 form a static sealed inner cavity 6 for accommodating and insulating the lubricating perfusate and generated wear particles.

The proximal holder 8 has two liquid passages, namely, a perfusion inlet pipeline 11 communicated with the perfusion inflow annul cavity 7 and a perfusion exhaust pipeline 12 communicated with the static sealed inner cavity 6. The distal holder 9 is provided with a perfusion insulation cavity 10, through which the flexible transmission shaft 1 passes to connect with the rotating element of the blood pump.

In preoperative preparation, the perfusion exhaust pipeline 12 is opened, and the perfusate enters the perfusion inflow annual cavity 7 from the perfusion inlet pipeline 11 and then flows into the perfusion insulation cavity 10 under the drive of the driving power means, such as a perfusion pump. At this time, the perfusion exhaust pipeline 12 is in an opened state, some of the perfusate in the perfusion insulation cavity 10 enters and fills the static sealed inner cavity (6) and is discharged through the perfusion exhaust pipeline 12 finally, and the rest of the perfusate enters the blood pump through the flexible transmission shaft 1;

During operation, the perfusion exhaust pipeline 12 is closed, all the perfusate in the perfusion insulation cavity 10 enters the blood pump instead of entering the static sealed inner cavity 6. At this time, the perfusion volume finally into the patient body is equal to the pump-out flow of the perfusion pump, and the total perfusate volume into the patient body can be known by monitoring the pump-out flow of a single perfusion pump. Meanwhile, the perfusate in the static sealed inner cavity 6 plays a role of lubricants and vibration buffer on the flexible shaft under high-speed rotation. Furthermore, closing the perfusion exhaust pipeline while keeping the perfusion flow unchanged may leads to increased hydraulic pressure in the perfusion insulation cavity 10, the perfusate in the static sealed inner cavity 6 is then prevented from flowing out, and the object of sealing generated wear particles in the static sealed inner cavity 6 is achieved.

The perfusate used in the examples of the present invention is heparin-containing glucose solution or normal saline.

Figure 4:
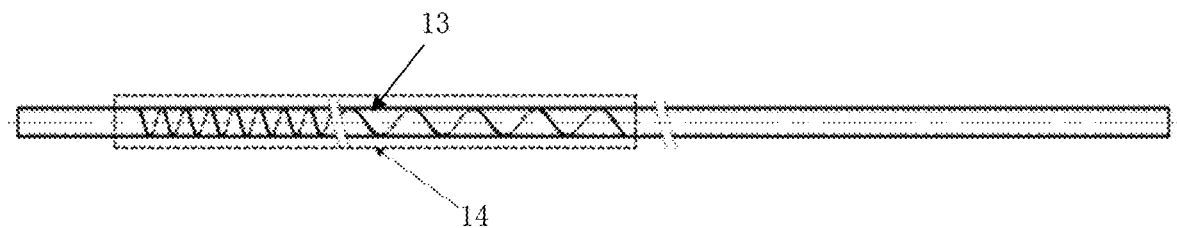
FIG. 4 is a schematic view showing a structure in which the flexible shaft adopts a flexible metal tube as an insulation layer in an embodiment of the present invention.

In the embodiment of the present invention, vibration and noise of the flexible shaft in high-speed operation are buffered by means of the constraint insulator. The outer sheath tube 5 is wrapped fully around but has no rigid connection with the constraint insulator. Gaps exist in the constraint insulator, and each of the constraint layers can make a slight vibratory movement in a radial direction under the protection of the outer sheath tube 5, while the perfusate fills all the gaps in the structure during operation. When the flexible transmission shaft 1 rotates, the inner constraint layer 2 may vibrate synchronously due to the bending angle and the sliding friction, the vibration energy of the inner layer is transmitted layer by layer in the constraint insulator and drives all the constraint layers, the insulation layers and the perfusate in the gaps to jointly vibrate while ensuring that the flexible transmission shaft 1 is centered in the inner constraint layer 2 all the time. At this time, the energy transmitted from the internal vibration is converted in part into the vibration kinetic energy of each constraint layer, and the rest is converted into the local turbulence kinetic energy in the perfusate, so that the vibration energy finally transmitted to the outer sheath tube is consumed and reduced, and the vibration amplitude of the outer sheath tube 5 is ultimately controlled. Furthermore, the insulation layer 3 in the constraint insulator may be sectioned to improve the passing performance of the product in a blood vessel during a clinical intervention by providing different support strengths at distal and proximal sections. Lower support strength is provided at the distal section to facilitate passage through a vascular lesion guided by a guide wire; higher support strength is provided at the proximal section to improve the pushing performance of a catheter, avoiding overall bent and congestion in the blood vessel due to insufficient support strength of the proximal catheter when passing through an aortic arch. Specifically, when the insulation layer 3 is composed of a flexible metal tube, the passing performance can be ensured by adding a threaded cut section 13 at the distal end, reducing the tube strength while adding a polymer sealing layer 14 outside the threaded cut section 13, as shown in FIG. 4, wherein the polymer sealing layer may adopt materials such as PE, PVC, PTFE and FEP. When the insulation layer 3 is composed of a thin-walled braided tube, the facilitated passing performance can be realized by increasing the braid density at the proximal end to enhance the support strength.

The flexible shaft of the present invention has a perfusion sealing structure, so that the controllability, stability and consistency of perfusion flow are further improved while shaft lubrication and wear particle sealing are realized.

Compared with the flushing technique in the prior art, the technical solution of the present invention is advantageous in that, firstly, the technical solution achieves an equivalent effect of lubricating the flexible shaft and insulating wear particles, and secondly, since sealed insulation is employed, it is not necessary to continuously flush the flexible shaft in use, therefore, less perfusate is needed in a continuous operation, replacement of perfusion bottles/perfusion bags happens less frequently in clinical use, on one hand, reducing the use of medical consumables, and on the other hand, reliving the medical staff from operational burdens.

In addition, in the continuous operation, the flexible shaft of the present invention has only one perfusion inlet and one perfusion outlet, so that the control of the perfusion flow finally entering the patient body can be realized through the closed-loop control of a single perfusion pump. Therefore, compared with the prior technical solution of flushing insulation which requires the precise collaboration of two perfusion pumps (one to pump in and the one to pumped out) and a plurality of sensors for flow control, the control logic is easier to implement, and flow stability, consistency and control reliability are better. Furthermore, higher-precision perfusion flow control facilitates the liquid management by the medical staff for the patient clinically.

Moreover, compared with the prior technical solution of the flexible shaft, the multiple constraint insulation layers can effectively insulate vibration and noise of the flexible shaft under high-speed rotation, so that the noise of the flexible shaft under a high-speed rotation at 50000 RPM can be controlled within 50 dB(A), and the external vibration amplitude can be controlled within 0.1 mm. On one hand, the risk of injury, bleeding or hematoma caused by high-frequency vibration at an intervention point in clinical use is reduced, and on the other hand, discomfort to the medical staff and the patient caused by continuous noise is avoided.

Although preferred embodiments the present invention are disclosed above, it is to be understood that the invention is not limited thereto, and that modifications and improvements may be made by those skilled in the art without departing from the spirit and scope of the invention, the scope of the invention is solely defined in the appended claims.

The invention claimed is:

1. A flexible shaft structure insulating wear particles by perfusion, comprising a flexible transmission shaft (1), a proximal holder (8) being provided at one end of the flexible transmission shaft (1), and a distal holder (9) being provided at the other end of the flexible transmission shaft (1), wherein a constraint insulator and an outer sheath tube (5) are provided outside the flexible transmission shaft (1), and the constraint insulator sequentially comprises an inner constraint layer (2), an insulation layer (3) and an outer constraint layer (4) from inside to outside;

a perfusion inflow annular cavity (7) is located between the outer constraint layer (4) and the outer sheath tube (5) and between the outer constraint layer (4) and the insulation layer (3), respectively, and a static sealed inner cavity (6) is located between the inner constraint layer (2) and the insulation layer (3) and between the inner constraint layer (2) and the flexible transmission shaft (1), respectively;

the proximal holder (8) is provided with a perfusion inlet pipeline (11) communicated with the perfusion inflow annular cavity (7) and a perfusion exhaust pipeline (12) communicated with the static sealed inner cavity (6); and the distal holder (9) is provided with a perfusion insulation cavity (10) through which the flexible transmission shaft (1) passes.

2. The flexible shaft structure insulating wear particles by perfusion according to claim 1, wherein the inner constraint layer (2) is composed of at least one braided spring tube or flexible metal tube coaxial with the flexible transmission shaft (1); the insulation layer (3) is composed of a flexible metal tube or a multilayer braided tube capable of insulating liquid coaxial with the inner constraint layer (2), and the outer constraint layer (4) is composed of at least one braided spring tube or flexible metal tube coaxial with the insulation layer (3).

3. The flexible shaft structure insulating wear particles by perfusion according to claim 2, wherein weights of the braided spring tubes composing the inner constraint layer (2) and the outer constraint layer (4) increase gradually from inside to outside.

4. The flexible shaft structure insulating wear particles by perfusion according to claim 2, wherein the insulation layer (3) is a flexible metal tube, a threaded cut section (13) is provided at a distal end of the flexible metal tube of the insulation layer (3), and the threaded cut section (13) is covered with a polymer sealing layer (14).

5. The flexible shaft structure insulating wear particles by perfusion according to claim 4, wherein the threaded cut section (13) is provided in sections, and thread pitches narrow gradually from a proximal end to a distal end.

6. The flexible shaft structure insulating wear particles by perfusion according to claim 2, wherein the insulation layer (3) is the multi-layer braided tube having a greater density at the proximal end than the density at the distal end.

7. A method for controlling the flexible shaft structure insulating wear particles by perfusion according to claim 1, comprising the steps of:

connecting the perfusion inlet pipeline (11) at the proximal end of the flexible transmission shaft (1) with a perfusion pump, passing the distal end of the flexible transmission shaft (1) through the perfusion insulation cavity (10) and then connecting with a blood pump;

before use, opening the perfusion exhaust pipeline (12), injecting a perfusate into the perfusion inflow annular cavity (7) through the perfusion inlet pipeline (11) with the perfusion pump, and then into the perfusion insulation cavity (10); enabling some of the perfusate in the perfusion insulation cavity (10) to enter and fill the static sealed inner cavity (6) and to be discharged through the perfusion exhaust pipeline (12) finally, and the rest of the perfusate to enter the blood pump through the flexible transmission shaft (1);

during use, closing the perfusion exhaust pipeline (12), enabling all the perfusate in the perfusion insulation cavity (10) to enter the blood pump instead of entering the static sealed inner cavity (6), and monitoring a pump-out flow of a single perfusion pump, which is a total volume of the perfusate entering a patient; and during use, keeping the perfusion exhaust pipeline (12) closed to increase a hydraulic pressure in the perfusion insulation cavity (10), so that the perfusate in the static sealed inner cavity (6) is prevented from flowing out and thus generated wear particles are retained in the static sealed inner cavity (6).

8. An artificially assisted blood pump device, comprising a rotating member for pumping blood and the flexible shaft structure insulating wear particles by perfusion according to claim 1, the flexible shaft structure being connected with the rotating member of the artificially assisted blood pump device.

\* \* \* \* \*